(12) United States Patent
Chang et al.

(10) Patent No.: US 11,903,678 B2
(45) Date of Patent: Feb. 20, 2024

(54) 3-DIMENSIONAL INTRAORAL SCANNER

(71) Applicant: MEDIT CORP., Seoul (KR)

(72) Inventors: Min Ho Chang, Seoul (KR); Soo Bok Lee, Seoul (KR); Kwang Jin Jang, Seoul (KR)

(73) Assignee: MEDIT CORP., Seoul (KR)

( * ) Notice: Subject to any disclaimer, the term of this patent is extended or adjusted under 35 U.S.C. 154(b) by 758 days.

(21) Appl. No.: 17/087,615

(22) Filed: Nov. 2, 2020

(65) Prior Publication Data

US 2021/0045637 A1 Feb. 18, 2021

Related U.S. Application Data

(63) Continuation of application No. PCT/KR2019/005242, filed on May 2, 2019.

(30) Foreign Application Priority Data

May 3, 2018 (KR) .......................... 10-2018-0051432

(51) Int. Cl.
*H04N 7/18* (2006.01)
*A61B 5/00* (2006.01)
(Continued)

(52) U.S. Cl.
CPC ........ *A61B 5/0088* (2013.01); *A61B 1/00194* (2022.02); *A61B 1/24* (2013.01);
(Continued)

(58) Field of Classification Search
CPC ..... A61B 5/0088; A61B 1/00194; A61B 1/24; A61B 5/0062; A61B 5/0073; A61B 5/0079; H04N 7/18; H04N 5/225; H04N 5/235
(Continued)

(56) References Cited

U.S. PATENT DOCUMENTS

| 5,771,067 A | * | 6/1998 | Williams | ............. | A61B 1/0615 |
| | | | | | 348/E5.025 |
| 5,897,509 A | * | 4/1999 | Toda | ........................ | A61B 1/24 |
| | | | | | 433/29 |

(Continued)

FOREIGN PATENT DOCUMENTS

| CN | 101822526 A | 9/2010 |
| CN | 204944451 U | 1/2016 |

(Continued)

OTHER PUBLICATIONS

International Search Report dated Aug. 2, 2019 for PCT/KR2019/005242.

(Continued)

*Primary Examiner* — Trang U Tran
(74) *Attorney, Agent, or Firm* — Insight Law Group, PLLC; Seung Lee

(57) ABSTRACT

The present invention relates to a three-dimensional oral scanner. In particular, the present invention comprises: a case which can be drawn in and out of an oral cavity and has an opening formed in a manner such that the shape of the inside of the oral cavity (hereinafter, abbreviated as "image") is introduced to the inside in the form of light through one end thereof; a pair of lenses disposed inside the case and spaced apart from each other in the width direction of the case so as to pass light incident from one end of the case in different paths; a pair of imaging boards having an imaging sensor for imaging the respective lights transmitted through the pair of lenses and disposed in close contact with a widthwise side wall and the other widthwise side wall of the case; and a pair of light path changing units arranged to change the respective paths of the lights transmitted through the pair of lenses toward the imaging board. As such, it is possible to manufacture an oral scanner to be slim overall, (Continued)

while providing the advantage of maximizing the utilization of the internal space of the oral scanner.

12 Claims, 7 Drawing Sheets

(51) Int. Cl.
    *A61B 1/00* (2006.01)
    *A61B 1/24* (2006.01)
(52) U.S. Cl.
    CPC .......... *A61B 5/0062* (2013.01); *A61B 5/0073* (2013.01); *A61B 5/0079* (2013.01)
(58) Field of Classification Search
    USPC .......................................................... 348/66
    See application file for complete search history.

(56) References Cited

U.S. PATENT DOCUMENTS

| | | | |
|---|---|---|---|
| 7,494,338 B2* | 2/2009 | Durbin | A61C 9/00 433/29 |
| 9,220,414 B2 | 12/2015 | Hack et al. | |
| 11,648,095 B2* | 5/2023 | Li | A61B 5/0088 348/66 |
| 11,684,268 B2* | 6/2023 | Christie | A61B 5/0088 600/478 |
| 2005/0090749 A1 | 4/2005 | Rubbert | |
| 2008/0082000 A1* | 4/2008 | Thoms | A61B 1/00177 600/476 |
| 2010/0238279 A1* | 9/2010 | Thoms | A61B 1/247 348/E7.085 |
| 2014/0272775 A1 | 9/2014 | Monty | |
| 2016/0000332 A1 | 1/2016 | Atiya et al. | |
| 2016/0005134 A1 | 1/2016 | von Gontard | |
| 2016/0051345 A1 | 2/2016 | Levin | |
| 2018/0098691 A1 | 4/2018 | Wang et al. | |
| 2018/0333232 A1* | 11/2018 | Lee | A61B 1/24 |

FOREIGN PATENT DOCUMENTS

| | | |
|---|---|---|
| JP | H7-323004 A | 12/1995 |
| JP | H8-029701 A | 2/1996 |
| JP | H11-56774 A | 3/1999 |
| JP | 2009-047894 A | 3/2009 |
| JP | 2011-087733 A | 5/2011 |
| JP | 5784381 B2 | 9/2015 |
| JP | 2016-522883 A | 8/2016 |
| KR | 10-1176770 B1 | 8/2012 |
| KR | 10-1371211 B1 | 3/2014 |
| KR | 10-2015-0057698 A | 5/2015 |
| KR | 10-2015-0111122 A | 10/2015 |
| KR | 10-2016-0017726 A | 2/2016 |
| KR | 10-2016-0133112 A | 11/2016 |
| KR | 10-1693158 B1 | 1/2017 |
| KR | 10-2018-0007660 A | 1/2018 |
| KR | 10-1838917 B | 3/2018 |
| KR | 10-1838917 B1 | 3/2018 |
| WO | 2010/090248 A1 | 8/2010 |

OTHER PUBLICATIONS

Non-final Office Action dated Aug. 18, 2023 for Chinese Application No. 201980030013.4.

Extended European Search Report dated Nov. 11, 2021 for European Application No. 19796257.4.

Japanese office action dated Dec. 21, 2022 for Japanese Application No. 2021-512346.

* cited by examiner

3-DIMENSIONAL INTRAORAL SCANNER

CROSS-REFERENCE TO RELATED APPLICATIONS

This application is a continuation application of International Application No. PCT/KR2019/005242, filed on May 2, 2019, which claims the benefit of and priority to Korean Patent Application No. 10-2018-0051432, filed on May 3, 2018, the content of which are incorporated herein by reference in their entirety.

TECHNICAL FIELD

The present disclosure relates to a three-dimensional (3D) intraoral scanner and, more particularly, to a 3D intraoral scanner among stereo vision-type intraoral scanners, the 3D intraoral scanner being able to increase the degree of freedom in the arrangement of imaging boards and maximize the usability of an internal space by disposing light path changing portions on front end portions of imaging sensors.

BACKGROUND ART

In general, an intraoral scanner is an optical device configured to be inserted into the oral cavity of a dental patient to scan the teeth in a non-contact manner in order to produce a 3D scanning model of rows of teeth.

In case of a single camera, 3D information is obtained using images captured in multiple views. As a related-art technology thereof, there is a method of obtaining distance information between an object and a camera using a coordinate system of images taken from different viewpoints. This method includes searching for identical objects from continuously-captured images by matching image information and then extracting the distance information of the object by projection. Thus, the related-art technology has problems, such as difficult processing of 3D information and increasing computational quantity. Recently, a stereo vision method using images captured from two or more cameras is widely used in intraoral scanners.

However, in the case of 3D data measurement using the stereo vision method, at least two cameras are required. Since two cameras must face an object to be measured in the same direction, the use of an internal space of the oral cavity scanner for accommodating two cameras is limited, which is problematic. The size of a scanner housing is increased. Thus, the design and fabrication of a device, such as the slim design of a portion substantially inserted into the oral cavity of a patient, are difficult, which is problematic.

In addition, Korean Patent No. 10-1838917 (published on Mar. 9, 2018; hereinafter, referred to as a "prior art") discloses the possibility of an optical system 210 able to use a stereo vision camera. However, the prior art merely proposes a scanner structure including a single condensing lens 212 and a single image sensing portion 120 in FIG. 11 of the specification of the prior art, but fails to disclose an internal structure of a stereo vision-based intraoral scanner.

DISCLOSURE

Technical Problem

An objective of the present disclosure is to provide a three-dimensional (3D) intraoral scanner among stereo vision-type intraoral scanners using two or more cameras, the 3D intraoral scanner being able to increase the degree of freedom in the arrangement of imaging boards and maximize the usability of an internal space by disposing light path changing portions on front end portions of imaging sensors.

Another objective of the present disclosure is to provide a 3D intraoral scanner able to easily obtain 3D oral cavity data including image state information of the interior of the oral cavity of a patient using two lenses disposed to be spaced apart from each other.

A further objective of the present disclosure is to provide a 3D intraoral scanner among stereo vision-type intraoral scanners, the 3D intraoral scanner having a structure by which a main housing to be grasped by a user and a tip housing to be substantially inserted into the oral cavity of a patient may be fabricated to be slimmer.

The technical problems of the present disclosure are not limited to the aforementioned description, and other technical problems not explicitly disclosed herein will be clearly understood by those skilled in the technical field, to which the present disclosure belongs, from the description provided hereinafter.

Technical Solution

According to an embodiment of the present disclosure for realizing the above objective, provided is a 3D intraoral scanner including: a housing insertable into and withdrawable from an oral cavity and having an open area allowing an internal shape (hereinafter, referred to as an image) of the oral cavity to be introduced as light thereinto through one end portion; a pair of lenses disposed within the housing and disposed to be spaced apart from each other in a transverse direction of the housing in order to allow the light entering from one end portion of the housing to pass along different paths therethrough; a pair of imaging boards respectively including an imaging sensor receiving the light that has passed through the pair of lenses to generate image information from the light and disposed in close contact with one and the other sidewalls of the housing in the transverse direction, respectively; and a pair of light path changing portions disposed to redirect light paths of the light, which has passed through the pair of lenses, toward the imaging boards.

Here, the pair of light path changing portions may be disposed to have reflector surfaces, the angles of which are determined such that rays of the light, which has passed through the pair of lenses, are incident to one surfaces of the imaging sensors provided on the imaging boards at predetermined angles, respectively.

The 3D intraoral scanner may further include a camera mounting portion having incoming light path portions therein, the incoming light path portions being provided between the pair of lenses and the imaging boards such that the light passes through incoming light path portions.

The pair of light path changing portions may be provided within the camera mounting portion.

The pair of light path changing portions may include reflector surfaces, the angles of which are determined such that rays of the light, which has passed through the pair of lenses, are incident to one surfaces of the imaging sensors provided on the imaging boards at predetermined angles, respectively, the reflector surfaces being inclined with respect to a longitudinal direction of the housing.

The 3D intraoral scanner may further include a light projector disposed within the housing, wherein the light projector radiates exiting light through between the pair of lenses through the open area provided in one end portion of the housing.

The focuses of the pair of lenses may be adjustable with respect to an image within the oral cavity.

The housing may include: a main housing accommodating the pair of lenses and a variety of electric components for driving the pair of imaging boards; and a tip housing coupled to one end portion of the main housing, and having the open area, an incoming light path portion guiding the light entering the main housing through the open area, and an exiting light path portion guiding light exiting the main housing through the open area.

The pair of lenses may be disposed such that one end portions thereof have a converging angle toward the tip housing and predetermined lengths thereof overlap the tip housing.

A reflective mirror may be provided in the open area provided in the tip housing, the reflective mirror reflecting the light entering the main housing and the light exiting the main housing through the open area along predetermined paths.

The pair of light path changing portions may respectively include a total reflection mirror.

The pair of light path changing portions may include a beam splitter.

Advantageous Effects

The 3D intraoral scanner according to an embodiment of the present disclosure may realize various effects as follows.

First, it is advantageously possible to increase the degree of freedom in the arrangement of the imaging boards and maximize the usability of the internal space of the housing by disposing the light path changing portions on the front end portions of the imaging sensors.

Second, there is an effect in that more accurate and reliable 3D oral cavity data may be obtained by integrating internal shapes (i.e. images) of the oral cavity obtained using the pair of lenses.

Third, since the main housing is provided such that the upper housing is simply detachably attached to the lower housing, components disposed within the housing may be very easily replaced.

DESCRIPTION OF REFERENCE NUMERALS OF DRAWINGS

Figure 1:
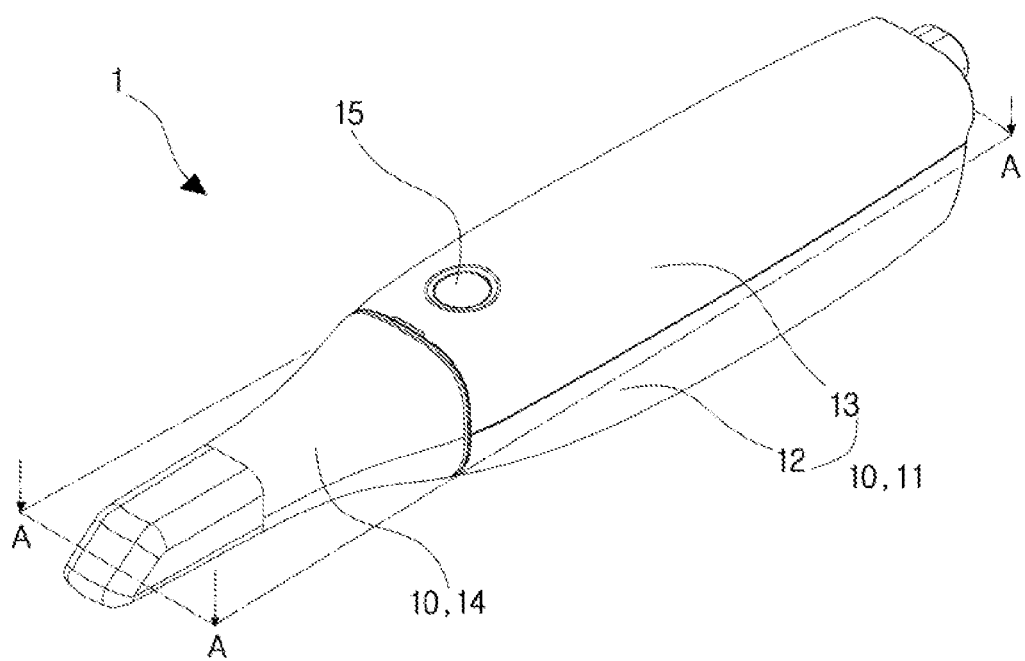
FIG. 1 is a perspective view illustrating a 3D intraoral scanner according to an embodiment of the present disclosure.

| | |
|---|---|
| 1: 3D intraoral scanner | 10: housing |
| 11: main housing | 12: lower housing |
| 13: upper housing | 14: tip housing |
| 16: open area | |
| 17: incoming/exiting light path portion | |
| 20: pair of lenses | 21: one lens |
| 22: the other lens | 31a, 32a: imaging board |
| 31b, 32b: imaging sensor | 41, 42: light path changing portion |
| 50: camera mounting portion | |
| 51, 52: incoming light path portion | |
| 53: exiting light path portion | |
| 60: reflective mirror | |
| 70: light projector | |

BEST MODE

Hereinafter, some embodiments of the present disclosure will be described in detail with reference to the accompanying illustrative drawings. It should be understood that, in designating elements of the drawings by reference numerals, the same elements will be designated by the same reference numerals although they are shown in different drawings. Further, in the following description of the present disclosure, a detailed description of known functions and configurations incorporated herein will be omitted in the situation in which the subject matter of the present disclosure may be rendered rather unclear thereby.

In addition, terms, such as first, second, A, B, (a), or (b), may be used herein when describing components of embodiments of the present disclosure. Each of these terminologies is not used to define an essence, order or sequence of a corresponding component but used merely to distinguish the corresponding component from other components. Unless otherwise specified, all terms including technical and scientific terms used herein have the same meaning as that commonly understood by those skilled in the technical field to which the present disclosure belongs. It will be further understood that terms, such as those defined in commonly used dictionaries, should be interpreted as having a meaning that is consistent with their meaning in the context of the relevant art, and will not be interpreted in an idealized or overly formal sense unless clearly defined herein.

Figure 2:
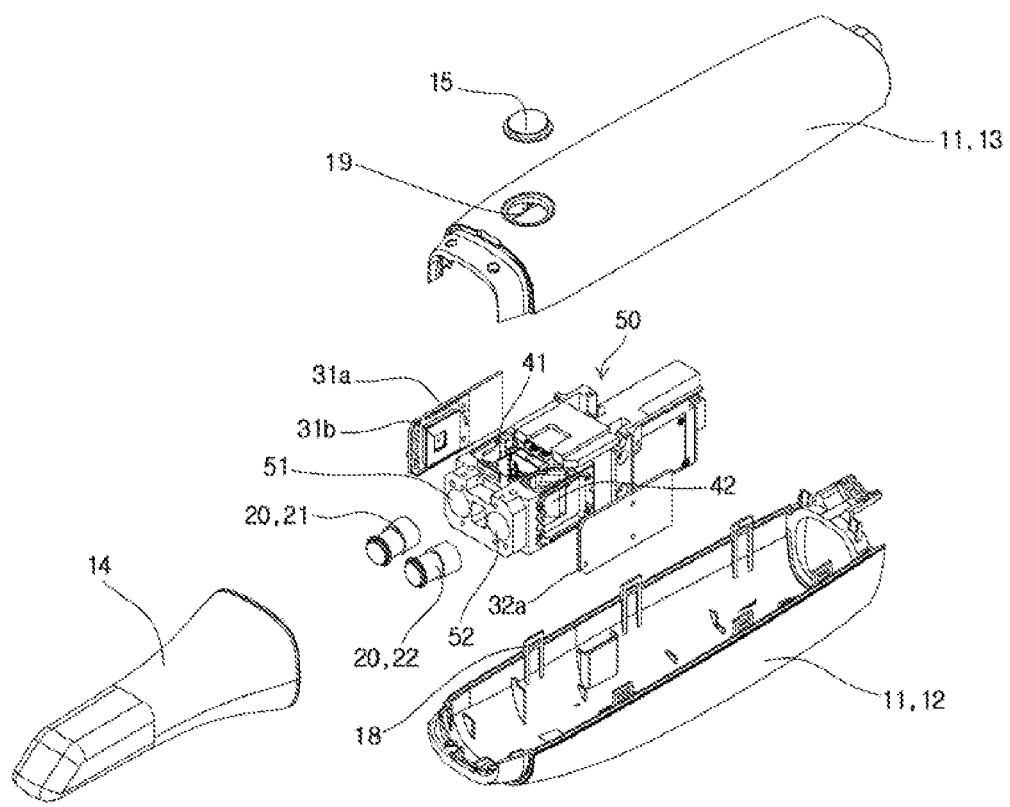
FIG. 2 is an exploded perspective view of FIG. 1.
Figure 3:
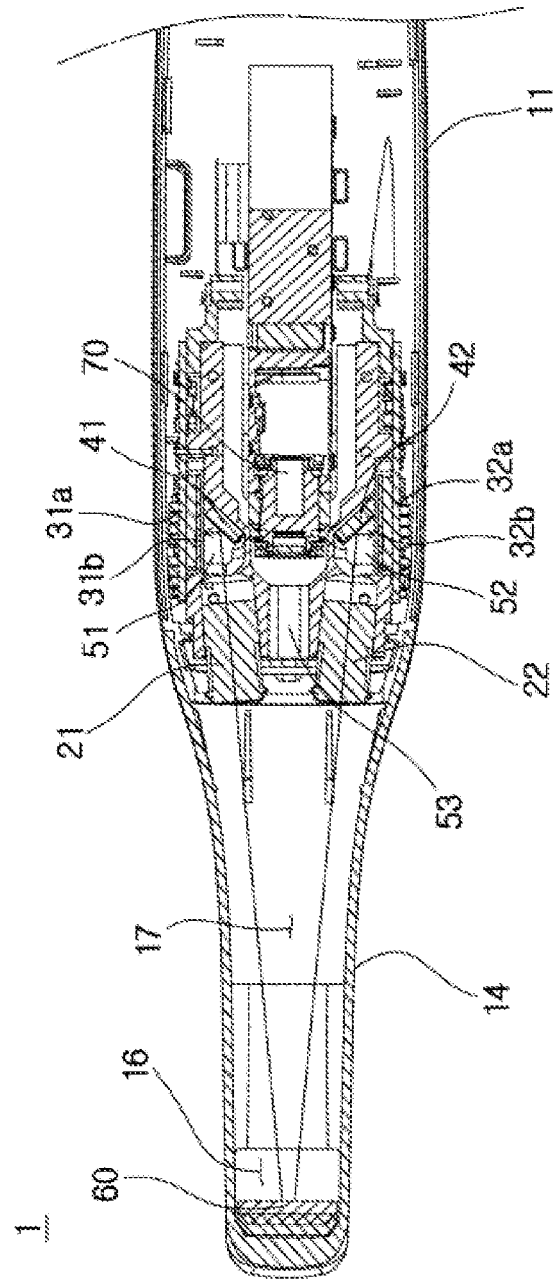
FIG. 3 is a cross-sectional view taken along the line A-A in FIG. 1.
Figure 4:
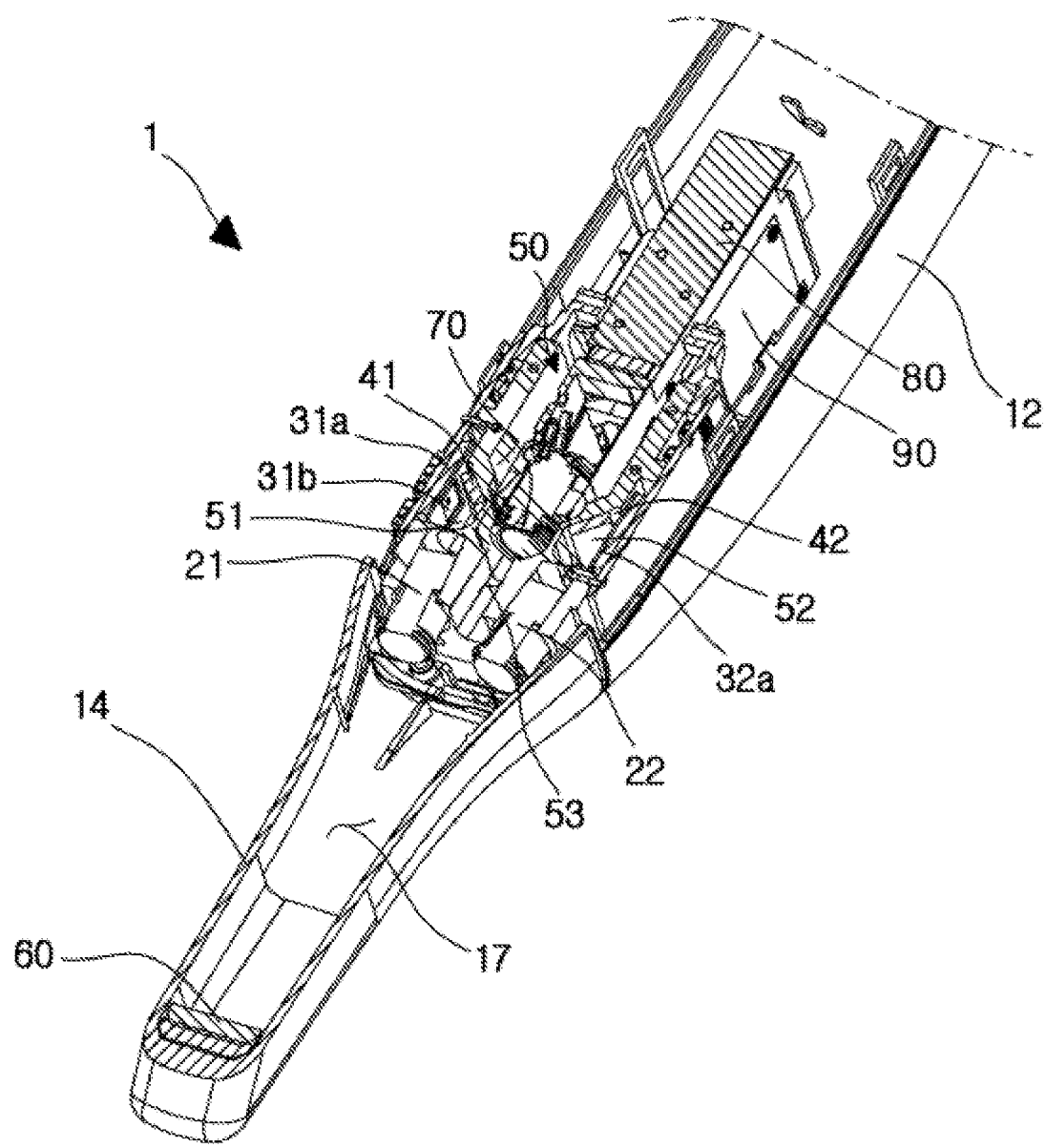
FIG. 4 is a cutaway perspective view taken along the line A-A in FIG. 1.

FIG. 1 is a perspective view illustrating a 3D intraoral scanner according to an embodiment of the present disclosure; FIG. 2 is an exploded perspective view of FIG. 1; FIG. 3 is a cross-sectional view taken along the line A-A in FIG. 1; and FIG. 4 is a cutaway perspective view taken along the line A-A in FIG. 1.

As illustrated in FIGS. 1 to 4, a 3D intraoral scanner according to an embodiment of the present disclosure includes a housing 10, a portion of which may be inserted into and withdrawn from an oral cavity.

A pair of lenses 20 may be disposed within the housing 10. The pair of lenses 20 may be spaced apart from each other in the transverse direction of the housing 10 so as to allow light incident thereto through one end portion of the housing 10 to travel along different paths. Here, "light" means radiation in the visible light range that is perceivable by human eyes, and indicates the internal shapes (hereinafter, referred to as "images") of the oral cavity of a patient to be measured.

However, the concept of "light" is not necessarily limited to the visible light range but does not exclude a case in which images to be obtained using the pair of lenses 20 are infrared (IR) image data.

Thus, the housing 10 may have an open area 16 in one end portion thereof, the open area 16 being open to allow an image in the form of light to enter the interior of the housing 10 therethrough. The open area 16 may be an entrance through which light external from the housing 10 enters the housing 10. Light entering through the open area 16 passes through the pair of lenses 20 along different light paths. Light that has passed through the pair of lenses 20 may be received by imaging sensors 31b and 32b provided in imaging boards 31a and 32a to be described later, thereby generating image information in the imaging sensors 31b and 32b.

In the 3D intraoral scanner according to an embodiment of the present disclosure, at least two pieces of image data of an image may be simultaneously obtained through the at least two lenses 20 using a stereo vision method. Thus, when the distance between the pair of lenses 20 and the focal distance of a target point taken using the lenses are obtained, 3D image data of the image may be obtained.

Although not specifically illustrated, the pair of lenses 20 may be provided such that the focus is adjustable with respect to an image of the interior of the oral cavity.

In this regard, the 3D intraoral scanner 1 according to an embodiment of the present disclosure may further include the imaging boards 31a and 32a having the imaging sensors 31b and 32b performing image processing to light that has passed through the pair of lenses 20. In addition, the 3D intraoral scanner 1 according to an embodiment of the present disclosure may further include a camera control board 80 on which electric components for controlling the operation of the pair of lenses 20 are mounted and a scanning control board 90 on which electric components for processing the scanned images are mounted.

As illustrated in FIGS. 1 to 3, the housing 10 serves to provide a space in which the pair of lenses 20, the imaging boards 31a and 32a, the camera control board 80, and the scanning control board 90 described above are accommodated.

More specifically, as illustrated in FIG. 2, the housing 10 includes a main housing 11 including a lower housing 12 having a space in which the above-described components are accommodated and an upper housing 13 provided above the lower housing 12, detachably coupled to the lower housing 12, and covering the above-described components.

Referring to FIG. 2, a plurality of hook fastening portions 18, each of which has a hook hole, are provided on the top portions of the periphery of the lower housing 12 to protrude upward predetermined lengths from the inner sidewalls, while a plurality of hook ribs 19 are provided on inner side portions of the periphery of the upper housing 13 so as to be fitted into the hook holes of the hook fastening portions 18, respectively.

Here, the main housing 11 not only is provided with the upper housing 13 and the lower housing 12 detachably coupled to each other in a simple manner but also provides a mounting space for facilitating attachment and detachment of a camera mounting portions 50 to be described later, thereby providing convenience that the upper housing 13 and the lower housing 12 may be easily detached when it is necessary to replace or repair components during use.

In addition, an operation button portion 15 may be provided on an outer peripheral portion of the upper housing 13. As illustrated in FIGS. 1 and 2, the operation button portion 15 may be disposed to extend through the upper housing 13 so as to switch a power switch (not shown) of the camera control board 80 coupled to the camera mounting portions 50 to be described later, thereby turning operation power on or off.

For example, when a user is pressing the operation button portion 15 with a finger, the operation power is in an on state, such that the interior of the oral cavity of a patient may be continuously scanned. In contrast, when the user detaches the finger from the operation button portion 15, the operation power is in an off state, such that the scanning of the oral cavity of the patient may be stopped.

In addition, the housing 10 may further include a tip housing 14 coupled to one end portion of the main housing 11. The tip housing 14 has the above-described open area 16 and an incoming/exiting light path portion 17 guiding light entering the main housing 11 through the open area 16 and exiting the main housing 11 through the open area 16.

Here, light (hereinafter, referred to as "incoming light") entering the main housing 11 through the open area 16 indicates the image of the interior of the oral cavity of the patient, while light (hereinafter, referred to as "exiting light") exiting the main housing 11 through the open area 16 indicates light radiated from a light projector 70 to be described later.

The internal structure of the tip housing 14 may form a light guide structure by which the incoming light and the existing light may be easily radiated into and from the housing 10. In addition, the open area 16 may be formed to be open in one direction perpendicular to the longitudinal direction of the tip housing 14, and a reflective mirror 60 to be described later may be disposed in the open area 16.

More specifically, when the tip housing 14 is defined as extending forward and backward in the longitudinal direction, the open area 16 may be formed to be open in one of the upward direction and the downward direction perpendicular to the longitudinal direction. In addition, the reflective mirror 60 is disposed in the open area 16 and serves to refract incoming light or exiting light so that the incoming light may enter or the exiting light may exit in one of the upward direction and the downward direction of the open area 16.

As described above, the pair of lenses 20 may be disposed such that one end portions thereof have a converging angle toward the tip housing 14 and predetermined lengths thereof overlap the tip housing 14.

That is, when the reflective mirror 60 is provided, incoming light is necessarily refracted by the reflective mirror 60 before entering the tip housing 14. Thus, the pair of lenses 20 may preferably be disposed to face the reflective mirror 60 with an angle at which the leading end portions thereof converge.

In addition, since the pair of lenses 20 are disposed such that one end portions thereof have a converging angle as described above, one end portions of the pair of lenses 20 may be position-designed to overlap an inner portion of the tip housing 14 that is fabricated to be substantially slim so as to be easily inserted into the oral cavity of the patient.

The arrangement of the pair of lenses 20 overlapping the tip housing 14 may provide a positional advantage capable of preventing any influence of external light through the distance between the tip housing 14 and the main housing 11.

In addition, the other end portions of the pair of lenses 20 may be provided to be connected to the camera mounting portions 50 fixedly disposed within the main housing 11.

In addition, as illustrated in FIGS. 2 to 4, the 3D intraoral scanner 1 according to an embodiment of the present disclosure may further include the light projector 70 disposed within the housing 10. The light projections 70 radiates exiting light through between the pair of lenses 20. That is, the light projections 70 radiates the exiting light through the open area 16 formed in one end portion of the housing 10.

The 3D intraoral scanner 1 according to an embodiment of the present disclosure proposes an optimal arrangement structure, by which the above-described components are disposed within the housing 10, such that the tip housing 14 is formed to be as long and slim as possible so as to be easily inserted into and withdrawn from the oral cavity of the patient while the main housing 11 is formed at the minimum thickness.

Here, in the 3D intraoral scanner 1 according to an embodiment of the present disclosure, the tip housing 14 is elongated so as to be easily inserted into the oral cavity of the patient. The 3D intraoral scanner may be more related to the design of locating the pair of lenses 20 and the imaging boards 31a and 32a having the imaging sensors 31b and 32b within the housing 10, in which the open area 16 and the pair of lenses 20 being relatively spaced apart and one end portions of the pair of lenses 20 being arranged to have a converging angle are considered.

More particularly, as illustrated in FIG. 2, the pair of lenses 20 may be provided within the housing 10 such that one end portions thereof protrude toward the tip housing 14, and the camera mounting portions 50 may be provided within the housing 10 such that the other end portions of the pair of lenses are inserted thereinto. In addition, the camera mounting portions 50 forms an optical waveguide serving as paths of incoming light that has passed through the pair of lenses 20 and existing light radiated from the light projector 70. The optical waveguide provided in the camera mounting portions 50 may be provided as darkrooms dividing the incoming light entering through the open area 16 and the exiting light radiated from the light projections 70 so that the incoming light and the exiting light do not interfere with each other.

That is, the optical waveguide may include an exiting light path portion 53 providing a light path including the tip housing 14 to the exiting light radiated from the light projector, one incoming light path portion 51 providing a light path to incoming light entering through one lens 21 of the pair of lenses 20, and the other incoming light path portion 52 providing a light path to incoming light entering through the other lens 22 of the pair of lenses 20.

Here, the exiting light path portion 53, one incoming light path portion 51, and the other incoming light path portion 52 may be provided to be partitioned from each other in order to ensure that light in each light path portion does not interfere with light in the remaining light path portions.

In addition, the light projector is located at the center of the other end portions of the pair of lenses 20 spaced apart from each other a predetermined distance in the transverse direction of the housing 10. The exiting light path portion 53 may be provided between one incoming light path portion 51 and the other incoming light path portion 52.

One incoming light path portion 51 and the other incoming light path portion 52 are provided to be in the same directions as the longitudinal directions of the lenses corresponding thereto, respectively, such that rays of incoming light entering from the pair of lenses 20 pass therethrough, respectively. Both one incoming light path portion 51 and the other incoming light path portion 52 may be provided to be open through one and the other side surfaces of the camera mounting portion 50.

Here, the imaging boards 31a and 32a to which the imaging sensors 31b and 32b are integrated may be vertically disposed in the top-bottom direction so as to be in close contact with one and the other sidewalls of the housing 10 in the transverse direction, respectively.

More specifically, one imaging board 31a may be disposed to be in close contact with the outer edge of one incoming light path portion 51 provided to be open through one side surface of the camera mounting portions 50 such that one imaging board 31a is disposed between the outer edge of one incoming light path portion 51 and one sidewall of the housing 10 in the transverse direction. In addition, the other imaging board 32a may be disposed to be in close contact with the outer edge of the other incoming light path portion 52 provided to be open through the other side surface of the camera mounting portions 50 such that the other imaging board 32a is disposed between the outer edge of the other incoming light path portion 52 and the other sidewall of the housing 10 in the transverse direction.

Here, the one imaging board 31a may be provided such that the imaging sensor 31b integrated thereto is exposed to one incoming light path portion 51, while the other imaging board 32a may be provided such that the imaging sensor 32b integrated thereto is exposed to the other incoming light path portion 52.

In addition, the 3D intraoral scanner 1 according to an embodiment of the present disclosure may further include a pair of light path changing portions 41 and 42 disposed to redirect the light paths of rays of light, which have passed through the pair of lenses 20, toward the imaging sensors 31b and 32b integrated to the imaging boards 31a and 32a, respectively.

One light path changing portion 41 of the pair of light path changing portions 41 and 42 may be one light path changing mirror 41 redirecting the light path of incoming light, which has passed through one incoming light path portion 51, toward the imaging sensor 31b integrated to one imaging board 31a. In addition, the other light path changing portion 42 of the pair of light path changing portions 41 and 42 may be the other light path changing mirror 42 redirecting the light path of incoming light, which has passed through the other incoming light path portion 52, toward the imaging sensor 32b integrated to the other imaging board 32a.

Here, each of the pair of light path changing portions 41 and 42 may include a total reflection mirror capable of totally reflecting light. However, each of the pair of light path changing portions 41 and 42 is not limited to the total reflection mirror but may include any optical element capable of totally reflecting light.

In addition, the pair of light path changing portions 41 and 42 may be implemented as a beam splitter. That is, the pair of light path changing portions 41 and 42 may be provided as a beam splitter to modify incoming light by dividing the incoming light into two beams at a predetermined ratio.

A main technical point of the 3D intraoral scanner 1 according to an embodiment of the present disclosure is to obtain 3D image data of the internal shape (i.e. image) of the oral cavity of the patient using the pair of lenses 20.

However, as described above, one end portions of the pair of lenses 20 (in a direction in which the tip housing 14 is provided in the drawings) must be disposed to have a converging angle to respectively face the reflective mirror 60 provided in the single open area 16, whereas each of the other end portions of the pair of lenses 20 (in a direction in which the light projections 70 is provided in the drawings) must have a structure allowing incoming light to pass therethrough in a linear direction.

Accordingly, the pair of imaging boards 31a and 32a must be disposed to be spaced apart from each other in the transverse direction of the housing 10 so as to be perpendicular to the linear directions of the other end portions of the pair of lenses 20, respectively. However, in this case, the thickness of the main housing 11 in the transverse direction may be increased by the length of the pair of imaging boards 31a and 32a. Such an increase in the thickness of the main housing 11 in the transverse direction may lead to a problem that would limit the slim design of the 3D intraoral scanner according to an embodiment of the present disclosure.

As described above, in the 3D intraoral scanner 1 according to an embodiment of the present disclosure, the incoming light path portions 51 and 52 are formed to be open through one and the other side surfaces of the camera mounting portion 50, the positions of the imaging boards 31a and 32a are determined such that the imaging boards 31a and 32a are disposed vertically between one and the other side surfaces of the camera mounting portions 50 and one and the other sidewalls of the housing 10, and the pair of light path changing portions 41 and 42 redirecting the light paths of incoming light that has passed through the pair of lenses 20 are provided. Accordingly, the main housing 11 may have a slim profile such that a tester may use the 3D intraoral scanner 1 by easily grasping the main housing 11 only with the thumb, the forefinger, and the middle finger.

The pair of light path changing portions 41 and 42 may be disposed to have reflector surfaces, the angles of which are determined such that rays of incoming light, which have passed through the pair of lenses 20, are incident to one surfaces of the imaging sensors 31b and 32b provided on the pair of imaging boards 31a and 32a at predetermined angles, respectively.

In this regard, the pair of light path changing portions 41 and 42 may be disposed such that the reflector surfaces thereof are inclined with respect to the longitudinal direction of the housing 10. That is, one light path changing mirror 41 may be provided such that incoming light, which has entered through one lens 21, enters through one incoming light path portion 51 and then is refracted by the reflector surface of one light path changing mirror 41 so as to be radiated to the imaging sensor 31b of one imaging board 31a. Likewise, the other light path changing mirror 42 may be provided such that incoming light, which has entered through the other lens 22, enters through the other incoming light path portion 52 and then is refracted by the reflector surface of the other light path changing mirror 42 so as to be radiated to the imaging sensor 32b of the other imaging board 32a.

In addition, the reflective mirror 60 may be provided in the open area 16 formed in the tip housing 14, as described above. The reflective mirror 60 serves to reflect incoming light entering the main housing 11 and existing light exiting the main housing 11 along predetermined paths.

In particular, the reflective mirror 60 facilitates the image-capturing using the pair of lenses 20 through the open area 16 open in a direction perpendicular to the longitudinal direction of the housing 10.

In addition, although not shown in the drawings, the reflective mirror 60 may be provided rotatable about a predetermined axis inside the tip housing 14. That is, the reflective mirror 60 may rotate about the predetermined axis so as to change a scanning area of an internal image of the oral cavity of the patient captured using the pair of lenses 20, thereby substantially changing the angle of incoming light entering through the open area 16.

In contrast, although not shown in the drawings, when the reflective mirror 60 is provided to be rotatable as described above, a mirror adjusting portion (not shown) for adjusting the angle of rotation of the reflective mirror 60 may be further provided on an outer portion of the housing 10. The mirror adjusting portion may be provided on the outer portion of the housing 10 as a button or a control lever.

In a case in which the mirror adjusting portion is provided as one or more buttons, when one of the buttons is pressed, the reflective mirror 60 may be rotated to a predetermined angle. In a case in which the mirror adjusting portion is provided as a control lever, when the control lever is pivoted to one side, the reflective mirror may be rotated in one direction so that the angle thereof is adjusted. When the control lever is pivoted to the other side, the reflective mirror 60 may be rotated in the other direction so that the angle thereof is adjusted.

As described above, it is possible to change the scanning area of the image by only operating the reflective mirror 60 to rotate without moving the housing 10, thereby advantageously increasing the scanning area in the same position.

This configuration of the rotating operation of the reflective mirror 60 may be significantly useful when the position of a tooth or teeth of the patient to be measured using the 3D intraoral scanner 1 according to an embodiment of the present disclosure is generally out of the scanning range.

More specifically, the tester inserts the 3D intraoral scanner 1 according to an embodiment of the present disclosure into the oral cavity of the patient in order to obtain 3D data of the teeth inside the oral cavity. Here, since the tip housing 14 is fabricated to be relatively slim, the 3D intraoral scanner may be located so that only the tip housing 14 is inserted into the oral cavity of the patient. However, in a case in which it is intended to obtain 3D data of a tooth located adjacent to the throat or a tooth located in a narrow space between teeth and lips, the tip housing 14 may be first inserted so that the leading end portion thereof is located around the tooth to be measured.

Afterwards, when the tooth that the tester intends to measure using the 3D intraoral scanner 1 according to an embodiment of the present disclosure in the oral cavity of the patient is out of the scanning area of the image obtained by the pair of lenses 20, it is possible to easily set the scanning area of the image of the tooth that is difficult to measure by adjusting the angle of the reflective mirror 60 using the mirror adjusting portion.

The operating state of the 3D intraoral scanner 1 having the above-described configuration according to the present disclosure will be described below in more detail with reference to the accompanying drawings (in particular, FIGS. 5 to 7).

Figure 5:
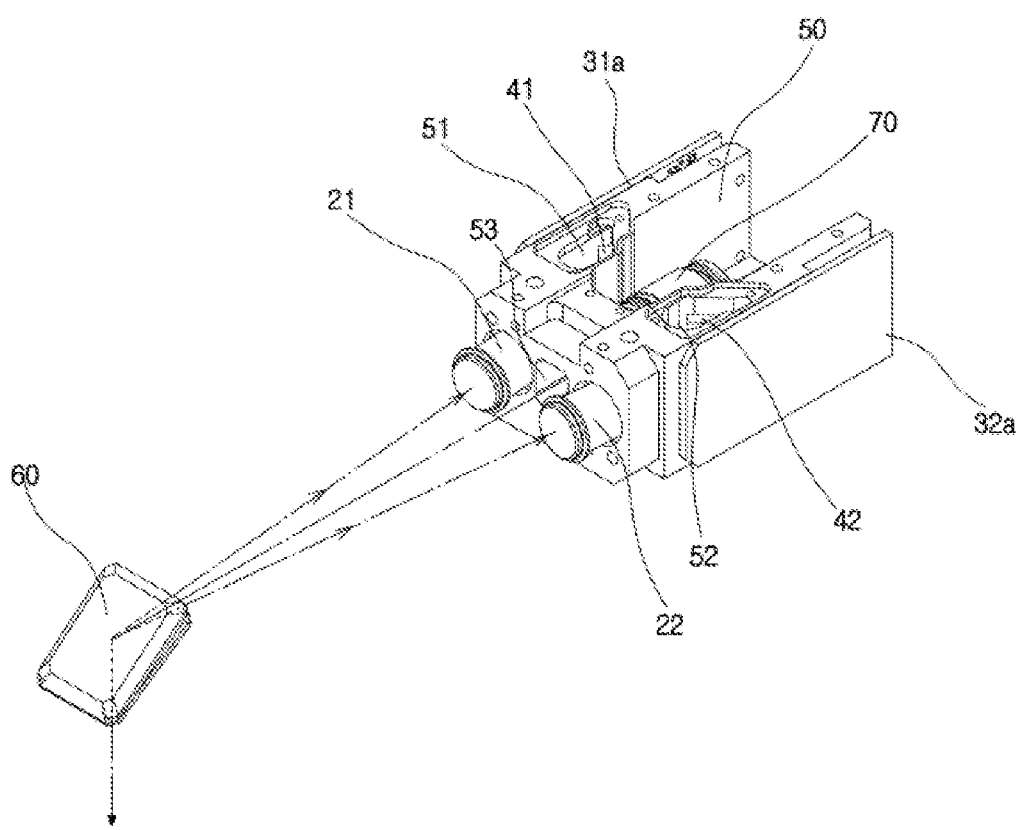
FIG. 5 is a perspective view illustrating light paths obtained using a pair of lenses in the configuration of FIG. 1.
Figure 6:
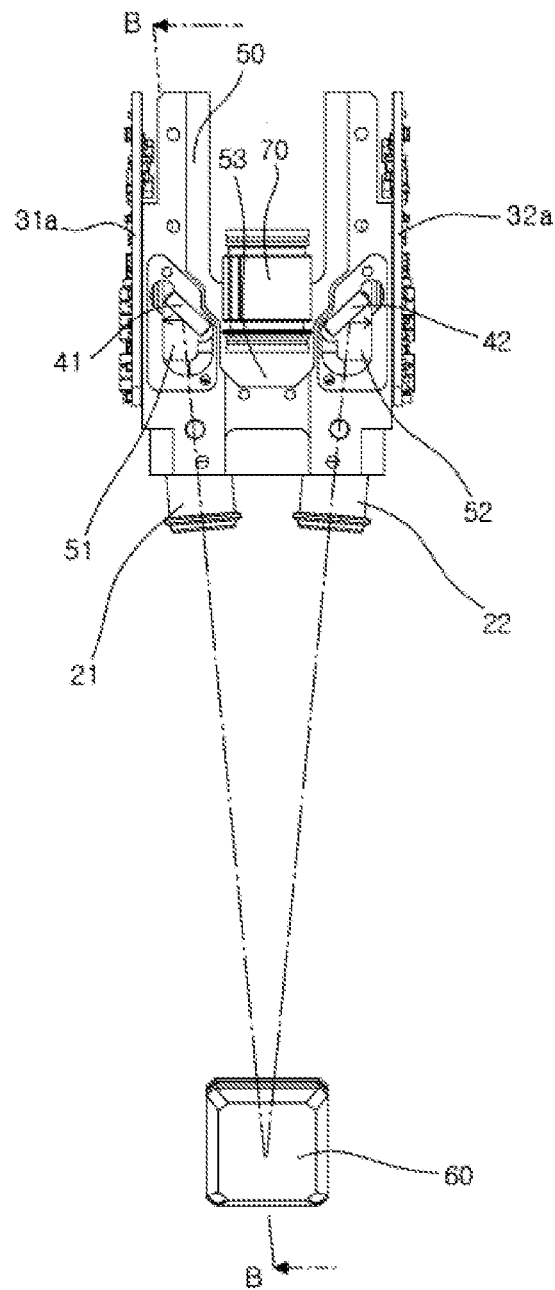
FIG. 6 is a plan view of FIG. 5.
Figure 7:
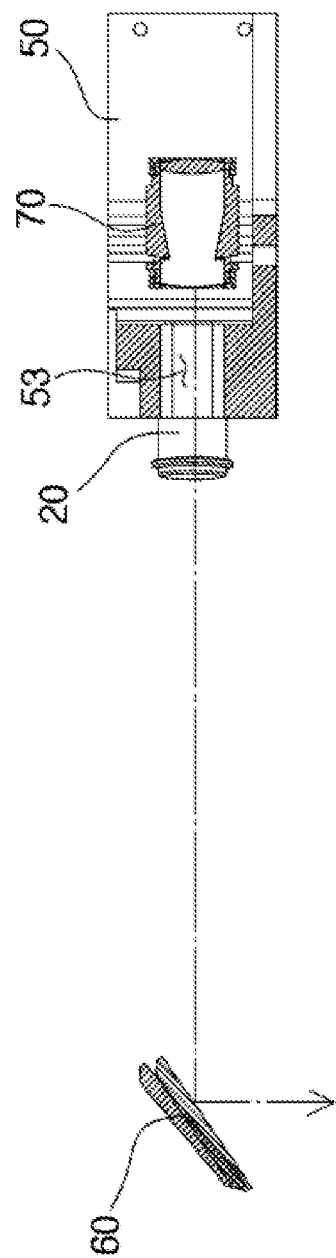
FIG. 7 is a cross-sectional view taken along the line B-B in FIG. 6.

FIG. 5 is a perspective view illustrating light paths obtained using the pair of lenses in the configuration of FIG. 1, FIG. 6 is a plan view of FIG. 5, and FIG. 7 is a cross-sectional view taken along the line B-B in FIG. 6.

The tester presses the operation button portion 15 provided on the top portion of the housing 10 in order to measure the interior of the oral cavity of the patient using the 3D intraoral scanner 1 according to an embodiment of the present disclosure.

Then, as illustrated in FIGS. 5 and 7, exiting light is radiated from the light projector 70. The exiting light radiated from the light projections 70 is radiated toward the open area 16 sequentially through the exiting light path portion 53 of the optical waveguide formed in the camera mounting portions 50 and the incoming/exiting light path portion 17 formed in the tip housing 14 and then is radiated into the oral cavity of the patient through the open area 16 by the reflective mirror 60.

At the same time, as illustrated in FIGS. 5 and 6, the pair of lenses 20 may be operated by the operation of the tester pressing the operation button portion 15 so as to obtain two pieces of image data having the same focus at a single point of the image.

Here, the image of the oral cavity of the patient exists in the form of light in response to exiting light. The image enters in the opposite sequence of the exiting light. That is, the image enters the interior of the tip housing 14 through the open area 16, is redirected by the reflective mirror 60, and is incident to the pair of lenses 20 substantially capturing images of the reflecting surface of the reflective mirror 60, through the incoming/exiting light path portion 17, the corresponding lenses, and the corresponding incoming light path portions 51 and 52 of the optical waveguide. Then, the image is radiated by the light path changing portions 41 and 42 to the imaging sensors 31*b* and 32*b* of the corresponding imaging boards 31*a* and 32*a*, so that two pieces of predetermined image data may be obtained. On the basis of the two pieces of image data obtained in this manner, 3D image data of the oral cavity of the patient may be easily obtained.

The above description provides an example of the technical idea of the present disclosure for illustrative purposes only, and those having ordinary skilled in the technical field to which the present disclosure pertains will appreciate that various modifications and changes are possible without departing from the essential features of the present disclosure.

Therefore, the embodiments disclosed in the present disclosure are intended not to limit but to illustrate the technical idea of the present disclosure, and the scope of the technical idea of the present disclosure is not limited by the embodiments. The scope of the present disclosure shall be construed on the basis of the accompanying claims, and all of the technical ideas included within the scope equivalent to the claims shall be construed as belonging to the scope of the present disclosure.

INDUSTRIAL APPLICABILITY

The present disclosure provides the 3D intraoral scanner among stereo vision-type intraoral scanners using two or more cameras, the 3D intraoral scanner being able to increase the degree of freedom in the arrangement of the imaging boards and maximize the usability of the internal space by disposing the light path changing portions on the front end portions of imaging sensors.

The invention claimed is:

1. A three-dimensional intraoral scanner comprising:
a housing insertable into and withdrawable from an oral cavity and having an open area allowing an internal shape (hereinafter, referred to as an image) of the oral cavity to be introduced as light thereinto through one end portion;
a pair of lenses disposed within the housing and disposed to be spaced apart from each other in a transverse direction of the housing in order to allow the light entering from one end portion of the housing to pass along different paths therethrough;
a pair of imaging boards respectively including an imaging sensor receiving the light that has passed through the pair of lenses to generate image information from the light and disposed in close contact with one and the other sidewalls of the housing in the transverse direction, respectively; and
a pair of light path changing portions disposed to redirect light paths of the light, which has passed through the pair of lenses, toward the imaging boards.

2. The three-dimensional intraoral scanner of claim 1, wherein the pair of light path changing portions are disposed to have reflector surfaces, the angles of which are determined such that rays of the light, which has passed through the pair of lenses, are incident to one surfaces of the imaging sensors provided on the imaging boards at predetermined angles, respectively.

3. The three-dimensional intraoral scanner of claim 1, further comprising a camera mounting portion having incoming light path portions therein, the incoming light path portions being provided between the pair of lenses and the imaging boards such that the light passes through incoming light path portions.

4. The three-dimensional intraoral scanner of claim 3, wherein the pair of light path changing portions are provided within the camera mounting portion.

5. The three-dimensional intraoral scanner of claim 1, wherein the pair of light path changing portions comprise reflector surfaces, the angles of which are determined such that rays of the light, which has passed through the pair of lenses, are incident to one surfaces of the imaging sensors provided on the imaging boards at predetermined angles, respectively, the reflector surfaces being inclined with respect to a longitudinal direction of the housing.

6. The three-dimensional intraoral scanner of claim 1, further comprising a light projector disposed within the housing, wherein the light projector radiates exiting light through between the pair of lenses through the open area provided in one end portion of the housing.

7. The three-dimensional intraoral scanner of claim 1, wherein the focuses of the pair of lenses are adjustable with respect to an image within the oral cavity.

8. The three-dimensional intraoral scanner of claim 1, wherein the housing comprises:
a main housing accommodating the pair of lenses and a variety of electric components for driving the pair of imaging boards; and
a tip housing coupled to one end portion of the main housing, and having the open area, an incoming light path portion guiding the light entering the main housing through the open area, and an exiting light path portion guiding light exiting the main housing through the open area.

9. The three-dimensional intraoral scanner of claim 8, wherein the pair of lenses are disposed such that one end portions thereof have a converging angle toward the tip housing and predetermined lengths thereof overlap the tip housing.

10. The three-dimensional intraoral scanner of claim 8, wherein a reflective mirror is provided in the open area provided in the tip housing, the reflective mirror reflecting the light entering the main housing and the light exiting the main housing through the open area along predetermined paths.

11. The three-dimensional intraoral scanner of claim 1, wherein the pair of light path changing portions respectively comprise a total reflection mirror.

12. The three-dimensional intraoral scanner of claim 1, wherein the pair of light path changing portions comprise a beam splitter.

* * * * *